United States Patent
Lamparth et al.

(10) Patent No.: US 11,793,732 B2
(45) Date of Patent: Oct. 24, 2023

(54) DENTAL MATERIALS BASED ON CYCLOPOLYMERIZABLE CROSSLINKERS

(71) Applicant: Ivoclar Vivadent AG, Schaan (LI)

(72) Inventors: Iris Lamparth, Grabs (CH); Norbert Moszner, Triesen (LI); Robert Liska, Schleinbach (AT); Christian Gorsche, Vienna (AT); Yohann Catel, Sevelen (CH); Gernot Peer, Vienna (AT)

(73) Assignee: Ivoclar Vivadent AG, Schaan (LI)

( * ) Notice: Subject to any disclaimer, the term of this patent is extended or adjusted under 35 U.S.C. 154(b) by 361 days.

(21) Appl. No.: 17/166,003

(22) Filed: Feb. 3, 2021

(65) Prior Publication Data
US 2021/0236388 A1 Aug. 5, 2021

(30) Foreign Application Priority Data
Feb. 5, 2020 (EP) .................. 20155585

(51) Int. Cl.
*A61K 6/54* (2020.01)
*A61K 6/887* (2020.01)

(52) U.S. Cl.
CPC .............. *A61K 6/54* (2020.01); *A61K 6/887* (2020.01)

(58) Field of Classification Search
CPC ...................................... A61K 6/887
See application file for complete search history.

(56) References Cited

U.S. PATENT DOCUMENTS

| | | | | |
|---|---|---|---|---|
| 4,041,063 A | * | 8/1977 | Buck | C07F 7/0838 558/442 |
| 4,889,948 A | * | 12/1989 | Mathias | C08F 16/32 564/201 |
| 5,145,374 A | | 9/1992 | Stansbury | |
| 5,380,901 A | | 1/1995 | Antonucci et al. | |
| 10,449,124 B2 | | 10/2019 | Murata et al. | |
| 2012/0214900 A1 | * | 8/2012 | Klee | A61K 6/30 525/327.4 |
| 2020/0085697 A1 | | 3/2020 | Fik et al. | |

FOREIGN PATENT DOCUMENTS

WO 20140040729 A1 3/2014

* cited by examiner

*Primary Examiner* — Michael F Pepitone
(74) *Attorney, Agent, or Firm* — Ann M. Knab; Thad McMurray

(57) ABSTRACT

Dental material which comprises at least one compound of formula I,

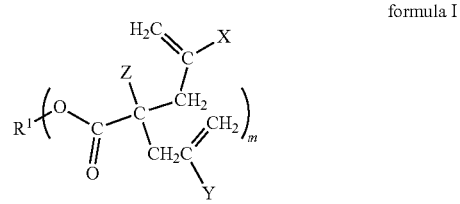

formula I in which $R^1$ is a linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein aliphatic hydrocarbon radicals can be interrupted by one or more urethane groups, ester groups, oxygen atoms and/or sulfur atoms; X, Y, Z independently of each other in each case are —$COOR^2$, —$CON(R^3R^4)$—, an aromatic $C_6$-$C_{10}$ hydrocarbon radical or CN, wherein $R^2$, $R^3$, $R^4$ in each case independently of each other is hydrogen, a linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein aliphatic hydrocarbon radicals can be interrupted by one or more oxygen atoms, and m is 2 or 3.

20 Claims, No Drawings

DENTAL MATERIALS BASED ON CYCLOPOLYMERIZABLE CROSSLINKERS

CROSS-REFERENCE TO RELATED APPLICATIONS

This application claims priority to European patent application No. 20155585.1 filed on Feb. 5, 2020, the disclosure of which is incorporated herein by reference in its entirety.

FIELD OF THE INVENTION

The invention relates to radically polymerizable compositions which are particularly suitable as dental materials, such as e.g. cements, filling composites, veneering materials and materials for producing inlays, onlays, crowns and bridges. The compositions contain a cyclopolymerizable crosslinker of formula I and are characterized by a low polymerization shrinkage.

BACKGROUND

The polymerization e.g. of vinyl compounds or (meth)acrylates is known to lead to a clear volume contraction, since during the formation of the polymer chains in each case one double bond and one Van-der-Waals bond in each monomer molecule are converted into two single bonds per chain growth step, i.e. the monomer building blocks in the polymer chain move closer together in comparison with the monomer phase. The polymerization shrinkage can lead to disadvantageous shrinkage stresses, to the formation of gaps or reduced substrate adhesion as well as to the impairment of the dimensional stability of shaped bodies. The change in density during the polymerization is decisively dependent on the molar mass and the molar volume of the monomers. Higher-molecular-weight monomers display a lower volume contraction than monomers with low molar mass.

In the dental field, the higher-molecular-weight dimethacrylates bis-GMA (molar mass=512.6 g/mol) and UDMA (molar mass=470.6 g/mol), which display a polymerization shrinkage $\Delta V_p$ of 6.0 (bis-GMA) and 6.1 vol.-% respectively, are widely used as relatively low-shrinkage monomers. However, as these monomers have a very high viscosity (bis-GMA: η=800-1000 Pa·s; UDMA: η=10 Pa·s) they are mostly used in a mixture with low-viscosity dimethacrylates with lower molar mass, which serve as diluent. Monomers with low molar mass, such as e.g. triethylene glycol dimethacrylate (molar mass=286.3 g/mol), however, have an increased polymerization shrinkage ($\Delta V_p$=14.5 vol.-%), which has a disadvantageous effect on the polymerization shrinkage of the material.

Various methods have been followed for the preparation of low-shrinkage polymerizates, such as e.g. the ring-opening polymerization of cyclic monomers or the use of thiol-ene resins.

In comparison with linear monomers the volume contraction in the case of the ring-opening polymerization of cyclic monomers is much lower, because in each case one covalent bond is opened and one covalent bond is formed per growth step here. Accordingly, cyclic monomers have attracted great interest as low-shrinkage matrix systems. However, cyclic monomers such as spiro orthocarbonates, cyclic ketene acetals or vinylcyclopropanes are much more expensive than methacrylates and sometimes have only limited storage stability.

The crosslinking thiol-ene polyaddition is characterized by an almost complete double-bond conversion and a much lower polymerization shrinkage than the radical polymerization of multifunctional methacrylates. Thus the volume contraction per polymerized (meth)acrylate double bond is approx. 22-23 cm³/mol, whereas in the case of the thiol-ene reaction the volume contraction is only 12-15 cm³ per mole of converted double bond. Moreover, the crosslinking thiol-ene polyaddition proceeds according to a step-growth mechanism and therefore has a significantly extended pre-gel phase in comparison with the dimethacrylate polymerization, which additionally leads to the reduction of the polymerization contraction stress. Unfortunately the use of thiol-ene resins is limited due to the very unpleasant odour of the thiols, the inherent flexibility of the thiol-ene polymers and due to the limited storage stability of the thiol-ene resins.

Cyclopolymerizable monomers have also been mentioned in connection with the reduction of the polymerization shrinkage. They are bi- or polyfunctional monomers, during the polymerization of which an intramolecular reaction accompanied by formation of 5- or 6-membered rings takes place in addition to the intermolecular chain growth reaction because of their specific monomer structure (cf. overview: D. Pasini, D. Takeuchi, Chem. Rev. 118 (2018) 8993-9057). Cyclopolymerization was described for the first time for quaternary diallylammonium salts in 1957 by Butler. Further examples of simple cyclopolymerizable monomers are acrylic and methacrylic anhydride, methyl allyl maleate and fumarate, diallyl phthalate and diethylene glycol bis(allyl carbonate).

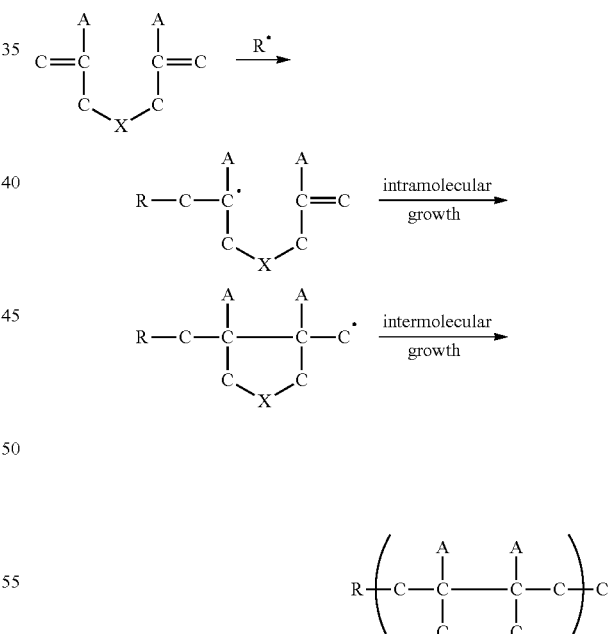

X = spacer : $CH_2$, O, NR
A = activating group

U.S. Pat. Nos. 5,145,374 and 5,380,901, which are hereby incorporated by reference, disclose dental adhesives and composites which contain cyclopolymerizable bis-acrylates (I) or oligomers (II). The materials are intended to have a low polymerization shrinkage.

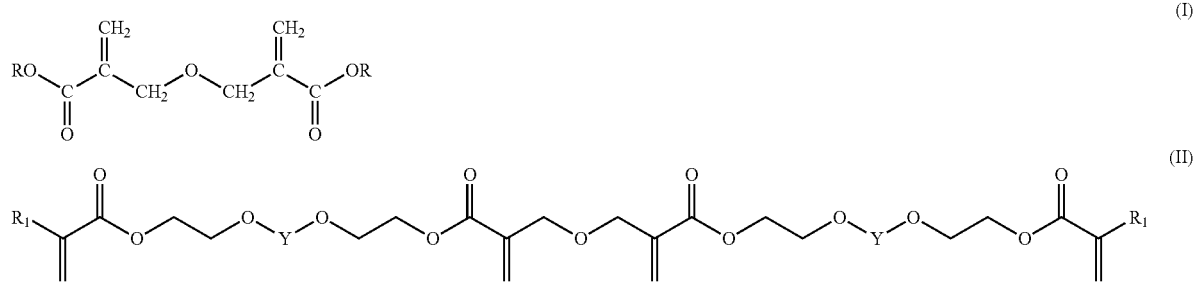

EP 3 335 688 A1 and corresponding U.S. Ser. No. 10/449,124, which is hereby incorporated by reference, disclose dental materials which contain cyclopolymerizable monomers, such as e.g. 1,6-diene-2-carboxylic acid (ester) and 1,5-diene-2-carboxylic acid (ester) monomers. Specifically, amongst others, α-allyloxymethacrylic acid cyclohexyl ester and methyl α-allyloxymethylmethacrylate are named. The materials are intended to have a flowability suitable for dental purposes before curing and a high mechanical strength, which is attributed to the ring formation during the cyclopolymerization, after curing.

WO 2014/040729 A1 discloses dental materials which contain N-allyl-substituted (meth)acrylamides, such as e.g. N,N-di(allylacrylamido)propane. The N-allyl-substituted (meth)acrylamides are intended to be characterized by a high hydrolysis stability, good copolymerizability with conventional (meth)acrylates, a low viscosity and excellent biocompatibility.

WO 2018/109041 A1 and corresponding US 2020085697, which is hereby incorporated by reference, disclose dental materials which contain N-allyl-substituted (meth)acrylamides with phosphoric acid ester groups, such as e.g. N-acryl-8-allylaminooctylphosphoric acid ester. The (meth)acrylamides are intended to be characterized by a high chemical purity and a high heat of polymerization in comparison with 10-methacryloyloxydecyl dihydrogen phosphate. Moreover, they are intended to yield advantageous mechanical properties after curing.

A disadvantage of the known cyclopolymerizable monomers in comparison with the (meth)acrylates usually used for the preparation of dental materials is their much lower reactivity during the radical polymerization, which is to be attributed to a degradative chain transfer mechanism. Moreover, their mechanical properties are unsatisfactory.

SUMMARY

The object of the invention is to provide dental materials which are characterized by a low polymerization shrinkage, good mechanical properties and a high reactivity during the radical polymerization, in particular during the photopolymerization.

DETAILED DESCRIPTION

The object is achieved according to the invention by dental materials which contain at least one compound of formula I:

formula I in which
- $R^1$ is an m-valent, linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be unsubstituted or substituted by one or more substituents, and wherein aliphatic hydrocarbon radicals can be interrupted by one or more, preferably 1 to 3, urethane groups, ester groups, oxygen atoms and/or sulfur atoms,
- X, Y, Z independently of each other in each case are —$COOR^2$, —$CON(R^3R^4)$, an aromatic $C_6$-$C_{10}$ hydrocarbon radical or —CN, wherein
- $R^2$, $R^3$, $R^4$ in each case independently of each other are hydrogen, a linear, branched or cyclic aliphatic $C_1$-$C_{30}$ hydrocarbon radical, preferably $C_1$-$C_{10}$ hydrocarbon radical, or an aromatic $C_6$-$C_{30}$ hydrocarbon radical, preferably $C_1$-$C_{10}$ hydrocarbon radical, wherein the aliphatic or aromatic hydrocarbon radical can be unsubstituted or substituted by one or more substituents and wherein aliphatic hydrocarbon radicals can be interrupted by one or more, preferably 1 to 3, oxygen atoms, and
- m is 2 or 3.

The substituents optionally present in the radicals $R^1$ to $R^4$ are preferably selected from chlorine, hydroxy and methoxy, wherein the radicals are optionally preferably substituted by 1 to 3 substituents. The radicals $R^1$ to $R^4$ are preferably not substituted by acid groups and are particularly preferably unsubstituted.

Compounds in which m is equal to 2 can be represented by formula Ia and compounds in which m is equal to 3 can be represented by formula Ib:

formula Ia

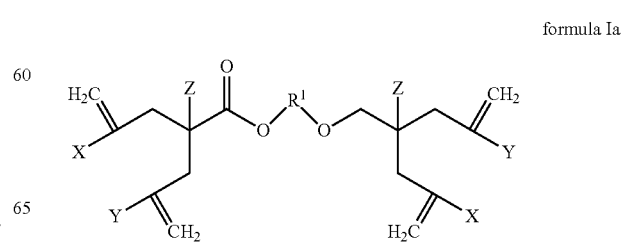

Formula Ib

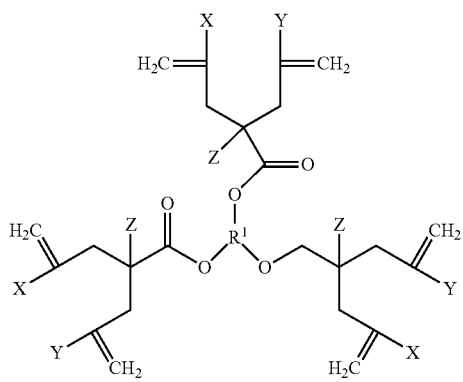

Formula I extends only to those compounds which are compatible with the theory of chemical valence. The indication that a radical is interrupted e.g. by one or more O atoms is to be understood to mean that these atoms or groups are inserted in each case into the carbon chain of the radical. These atoms or groups are thus bordered on both sides by C atoms and cannot be terminal. $C_1$ radicals cannot be interrupted, branched or cyclic. Corresponding to the usual nomenclature, by aromatic hydrocarbon radicals is also meant those radicals which contain aromatic and non-aromatic groups. A preferred aromatic radical is, for example, the diphenylpropane radical.

The groups X, Y and Z can be identical or different. Preferably, X and Y have the same meaning, compounds in which X, Y and Z are identical are particularly preferred.

The variables preferably have the following meanings:

$R^1$ a linear, branched or cyclic aliphatic $C_1$-$C_{20}$ hydrocarbon radical, which can be interrupted by one or more, preferably 1 to 3, urethane groups, ester groups and/or oxygen atoms, X, Y, Z independently of each other in each case —$COOR^2$, an aromatic $C_6$-$C_{10}$ hydrocarbon radical or —CN, $R^2$ a linear, branched or cyclic aliphatic $C_1$-$C_{10}$ hydrocarbon radical, which can be interrupted by one or more, preferably 1 to 3, oxygen atoms, and m 2 or 3.

Compounds of formula I in which the variables have the following meanings are particularly preferred:

$R^1$ a linear, branched or cyclic aliphatic $C_1$-$C_{12}$ hydrocarbon radical, preferably a saturated, branched or preferably linear $C_2$ to $C_8$ hydrocarbon radical, which can be interrupted by one or more, preferably 1 to 3, oxygen atoms, and is preferably not interrupted, X, Y, Z independently of each other in each case —$COOR^2$ or phenyl, preferably —$COOR^2$, $R^2$ a linear or branched $C_1$-$C_4$ hydrocarbon radical, preferably ethyl, and m 2 or 3, preferably 2.

The preferred, particularly preferred and quite particularly preferred definitions given for the individual variables can be selected in each case independently of each other. Compounds in which all the variables have the preferred, particularly preferred and quite particularly preferred definitions are naturally particularly suitable according to the invention.

The hydrocarbon radicals are in all cases preferably saturated hydrocarbon radicals. This applies both to the general definition and to the preferred and in particular also to the particularly preferred compounds of formula I.

The cyclopolymerizable compounds of formula I are not known and can be prepared analogously to similar compounds (cf. Bourgeois, J.-P.; Echegoyen, L.; Fibbioli, M.; Pretsch, E.; Diederich, F., Angewandte Chemie International Edition 1998, 37 (15), 2118-2121 and Gregg, Z. R.; Griffiths, J. R.; Diver, S. T., Organometallics 2018, 37 (10), 1526-1533). In the first step, a multifunctional alcohol is esterified with an acid chloride under basic conditions. In the second step, after deprotonation it is reacted with a vinyl source based on 2-chloromethyl alkenes.

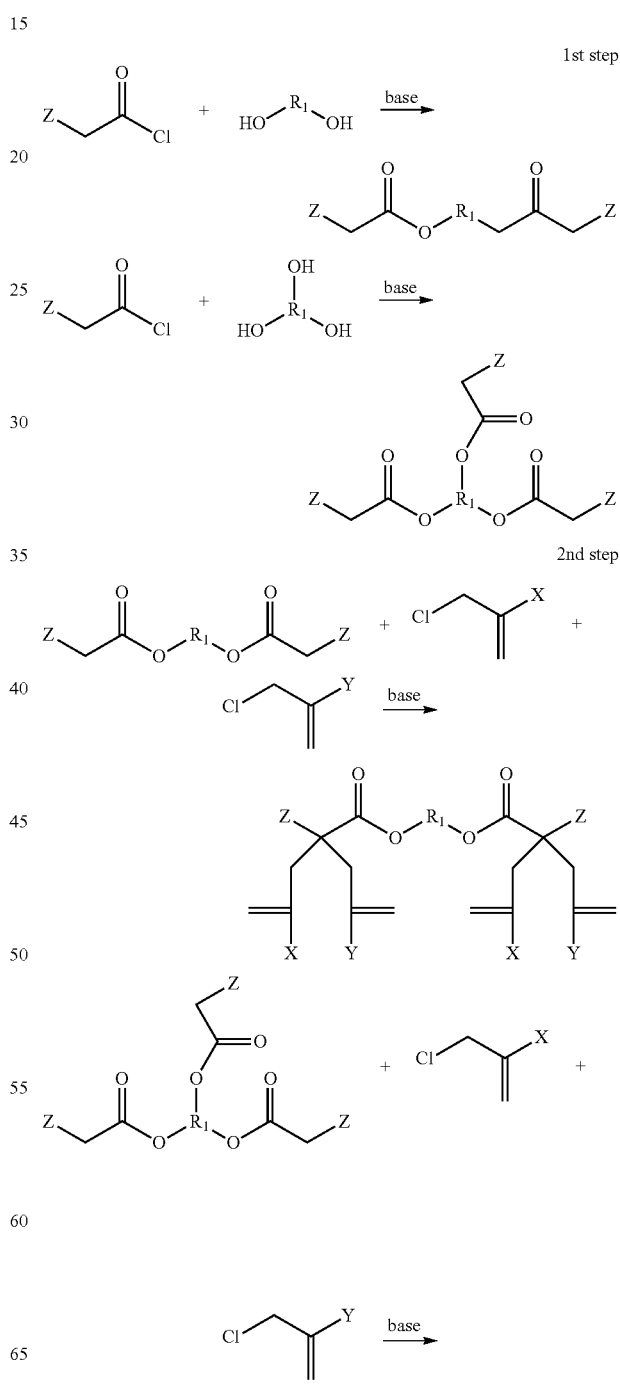

1st step

2nd step

-continued
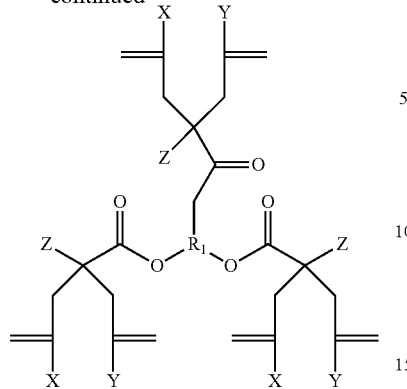
A specific example is:
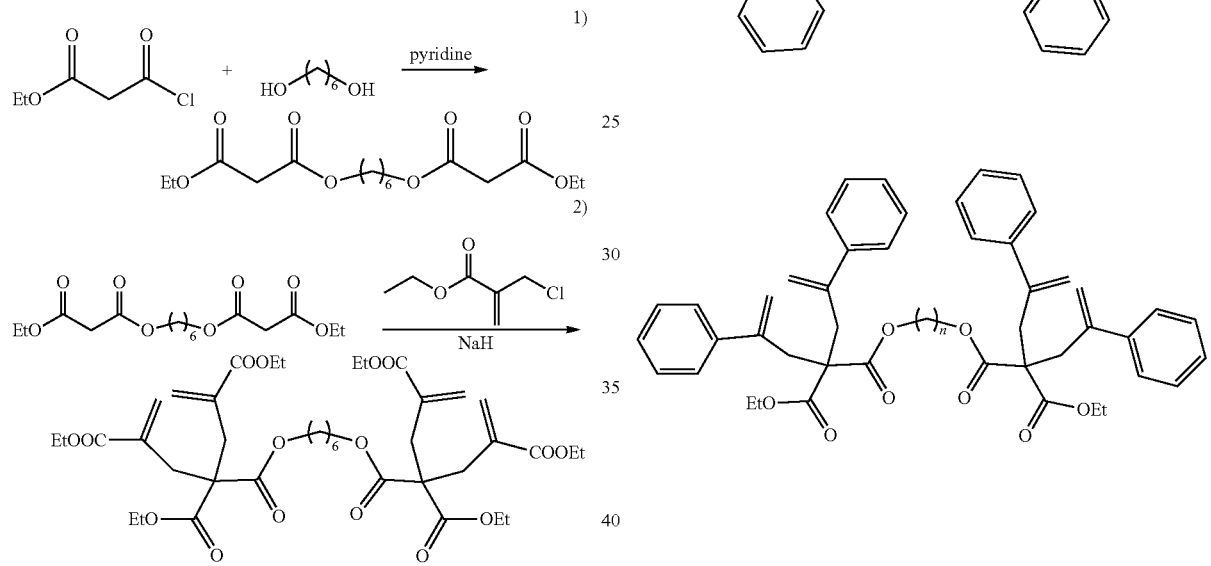
Preferred compounds of formula I according to the invention are:
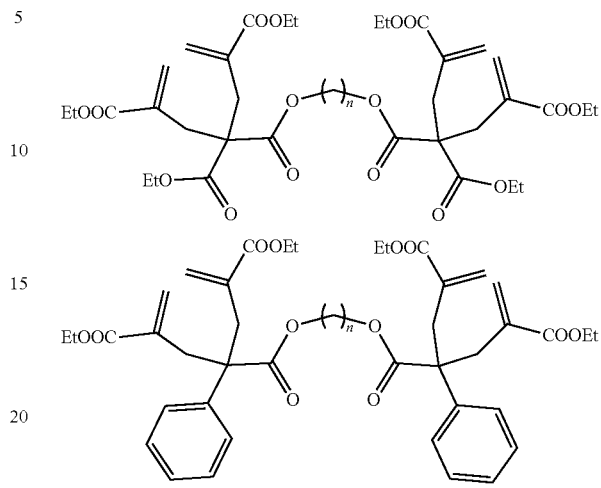
with n=1 to 15
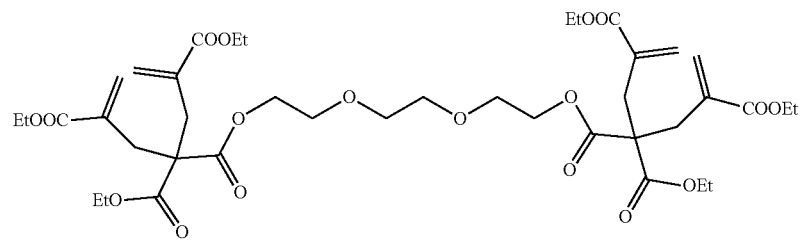
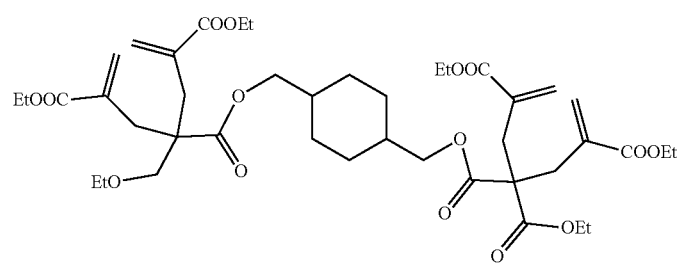

-continued
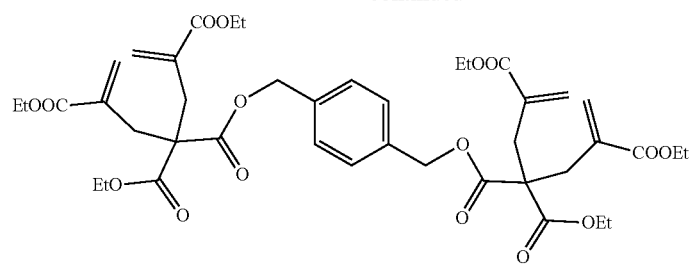
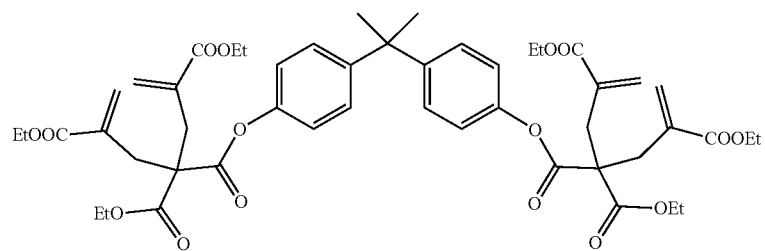
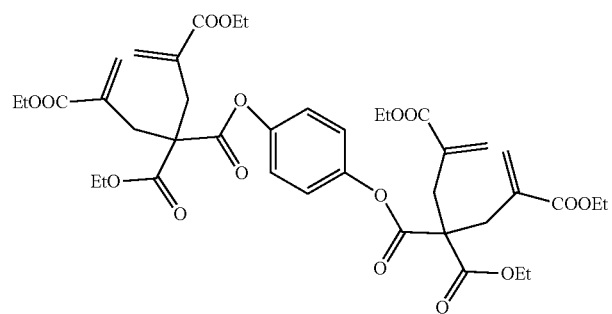
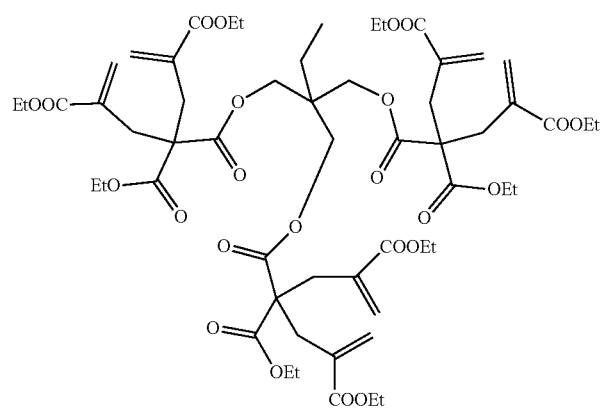 [SMILES: C=C(CC(CC(=C)C(=O)OCC)(C(=O)OCC)C(=O)OCC(CC)(COC(=O)C(CC(=C)C(=O)OCC)(CC(=C)C(=O)OCC)C(=O)OCC)COC(=O)C(CC(=C)C(=O)OCC)(CC(=C)C(=O)OCC)C(=O)OCC)C(=O)OCC]

Particularly preferred compounds of formula Ia are the following substances:

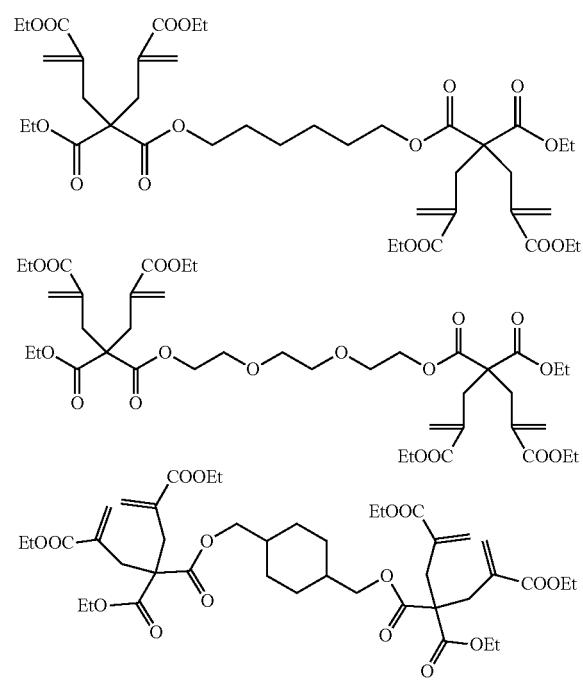

A preferred compound of formula Ib is:

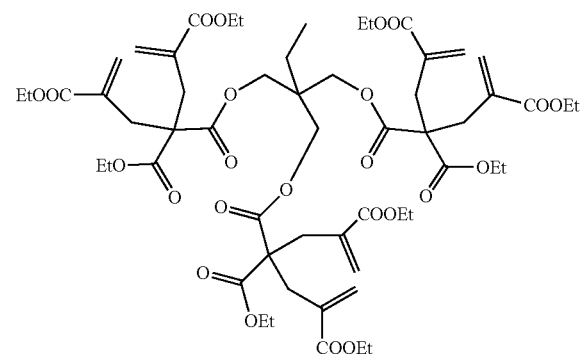 [SMILES: C=C(CC(CC(=C)C(=O)OCC)(C(=O)OCC)C(=O)OCC(CC)(COC(=O)C(CC(=C)C(=O)OCC)(CC(=C)C(=O)OCC)C(=O)OCC)COC(=O)C(CC(=C)C(=O)OCC)(CC(=C)C(=O)OCC)C(=O)OCC)C(=O)OCC]

The compounds of formula I according to the invention contain four or six polymerizable groups and have cross-linking properties. They are characterized by a high reactivity of the cyclopolymerizable groups during the radical polymerization and can be copolymerized well with conventional dental monomers, in particular with di(meth) acrylates. Because of their high reactivity they can, for example, also be homopolymerized, unlike the known, cyclopolymerizable N,N-disubstituted methacrylamides. During the homo- and copolymerization of the compounds of formula I according to the invention polymer networks with good mechanical properties are obtained, which are advantageous for dental applications.

In addition, the compounds of formula I according to the invention are characterized by a reduced polymerization shrinkage stress and a low polymerization shrinkage as a result of the cyclopolymerization. They thus make it possible to utilize these advantages for dental applications without impairing other properties likewise essential for dental purposes, such as in particular the mechanical properties.

The compounds of formula I are particularly suitable for the preparation of dental materials, for example for the preparation of coating or veneering materials, dental cements and in particular filling composites. They are furthermore suitable for the preparation of materials for the production or repair of dental prostheses, inlays, onlays, crowns or bridges. However, they are also suitable for the preparation of radically polymerizable materials and thermosets for other purposes. The (dental) materials according to the invention preferably contain 0.5 to 70 wt.-%, particularly preferably 1 to 60 wt.-% and quite particularly preferably 3 to 50 wt.-% of at least one compound of formula I, relative to the total mass of the material.

The compounds of formula I according to the invention are preferably used in combination with one or more polymerizable, mono- or multifunctional monomers (comonomers). By monofunctional monomers is meant compounds with one, and by multifunctional monomers is meant compounds with two or more, preferably 2 to 4 radically polymerizable groups. Preferred comonomers are radically polymerizable monomers.

Dental materials which contain at least one mono- or multifunctional (meth)acrylate as radically polymerizable comonomer are preferred according to the invention. Materials which are to be cured intraorally preferably contain mono- and/or multifunctional methacrylates as radically polymerizable monomer. Methacrylates are therefore particularly preferred as comonomers. It was surprisingly found that the compounds of formula I according to the invention can be copolymerized well with conventional (meth)acrylates.

Preferred multifunctional methacrylates are dimethacrylates, in particular bisphenol A dimethacrylate, 2,2-bis[4-(2-hydroxy-3-methacryloyloxypropyl)phenyl]propane (bis-GMA; an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)phenyl]propane) (SR-348c; contains 3 ethoxy groups), 2,2-bis[4-(2-methacryloyloxypropoxy)phenyl]propane, 1,6-bis-[2-methacryloyloxy-ethoxycarbonylamino]-2, 2,4-trimethylhexane (UDMA; an addition product of 2-hydroxyethyl methacrylate and 2,2,4-trimethylhexamethylene-1,6-diisocyanate), di-, tri- and tetraethylene glycol dimethacrylate, trimethylolpropane trimethacrylate, pentaerythritol tetramethacrylate, glycerol di- and glycerol trimethacrylate, 1,4-butanediol dimethacrylate, 1,10-decanediol dimethacrylate ($D_3MA$), 1,12-dodecanediol dimethacrylate, bis(methacryloyloxymethyl)tricyclo-[5.2.1.0$^{2,6}$] decane (DCP) and mixtures thereof. Particularly preferred multifunctional methacrylates are bis-GMA, SR-348c, UDMA, $D_3MA$, DCP, triethylene glycol dimethacrylate and mixtures thereof.

Multifunctional monomers, in particular methacrylates, are preferably used in a total quantity of at most 70 wt-%, particularly preferably 1.5 to 60 wt.-% and quite particularly preferably 2 to 50 wt.-%, relative to the total mass of the material.

Monofunctional monomers preferred according to the invention are monomethacrylates. Particularly preferred monomethacrylates are benzyl methacrylate, tetrahydrofurfuryl methacrylate, isobornyl methacrylate, p-cumyl-phenoxyethylene glycol methacrylate (CMP-1E), 2-(2-biphenyloxy)-ethyl methacrylate and mixtures thereof.

Monofunctional monomers, in particular methacrylates, are preferably used in a total quantity of at most 10 wt.-%, particularly preferably 0 to 10 wt-% and quite particularly preferably 0 to 5 wt.-%, relative to the total mass of the material.

Mono- and multifunctional acrylates are furthermore also suitable as comonomers. Preferred multifunctional acrylates are ethylene glycol diacrylate, hexanediol diacrylate, tripropylene glycol diacrylate, ethoxylated bisphenol A diacrylate, polyethylene glycol 200 diacrylate, trimethylolpropane triacrylate, pentaerythritol tetraacrylate and mixtures thereof.

Mono- and multifunctional acrylates are preferably used in a total quantity of at most 50 wt.-%, preferably 0 to 50 wt.-% and particularly preferably 0 to 30 wt.-%, relative to the total mass of the dental material.

The total quantity of comonomers is preferably at most 70 wt.-%, particularly preferably 1.5 to 60 wt.-% and quite particularly preferably 2 to 50 wt.-%, relative to the total mass of the material.

The compositions according to the invention preferably contain an initiator for the radical polymerization, e.g. for the polymerization by UV light, by visible light, a thermal initiator and/or a redox initiator. Photoinitiators are particularly preferred, photoinitiators which are activated by visible light are quite particularly preferred.

Norrish type I initiators, such as e.g. benzil dimethyl ketal, benzoin ether, hydroxyphenyl ketones, dialkoxy acetophenones, benzoyl cyclohexanol, trimethylbenzoylphosphine oxide and morpholino phenyl amino ketones, are preferred as UV photoinitiators. Preferred Norrish type II UV initiators are mixtures of e.g. benzophenone or thioxanthone derivatives with H donors such as alcohols, or thiols, or electron donors such as amines.

Preferred bimolecular photoinitiators for the visible range are α-diketones and derivatives thereof, such as 9,10-phenanthrenequinone, 1-phenyl-propane-1,2-dione, diacetyl or 4,4'-dichlorobenzil, as well as mixtures thereof. Camphorquinone (CQ) and 2,2-dimethoxy-2-phenyl-acetophenone are particularly preferred, and α-diketones in combination with amines as reducing agent are quite particularly preferred, such as e.g. 4-(dimethylamino)-benzoic acid ethyl ester (EDMAB), N,N-dimethylaminoethyl methacrylate, N,N-dimethyl-sym.-xylidine or triethanolamine. Preferred Norrish type I photoinitiators for the visible range are bisacylphosphine oxides. Monoacyltrialkylgermanium, diacyldialkylgermanium and tetraacylgermanium compounds, such as e.g. benzoyltrimethylgermane, dibenzoyldiethylgermane, bis(4-methoxybenzoyl)diethylgermane (Ivocerin®), tetrabenzoylgermane or tetrakis(o-methylbenzoyl)germane, are particularly preferred.

Moreover, mixtures of the different photoinitiators can advantageously also be used, such as e.g. bis(4-methoxybenzoyl)diethylgermane or tetrakis(o-methylbenzoyl)germane in combination with camphorquinone and 4-dimethylaminobenzoic acid ethyl ester.

Preferred thermal initiators are azo compounds, such as e.g. 2,2'-azobis(isobutyronitrile) (AIBN), azobis-(4-cyanovaleric acid) or peroxides, such as e.g. dibenzoyl peroxide, dilauroyl peroxide, tert-butyl peroctoate, tert-butyl perbenzoate or di-(tert-butyl) peroxide. To accelerate the initiation by means of peroxides, combinations of peroxides with aromatic amines can also be used. Preferred combinations are combinations of dibenzoyl peroxide with an amine, preferably an N,N-dialkyl-substituted aromatic amine, which is substituted in the p-position, such as N,N-dimethyl-p-toluidine, N,N-dihydroxyethyl-p-toluidine, p-dimethylaminobenzoic acid ethyl ester.

Combinations of a photoinitiator with a thermal or preferably a redox initiator are suitable for a dual curing. Preferred redox initiators for the dual curing are systems which contain a peroxide and a reducing agent, such as e.g. ascorbic acid, a barbiturate or a sulfinic acid, or a hydroperoxide in combination with a reducing agent and optionally catalytic quantities of metal ions, such as e.g. a mixture of cumene hydroperoxide, a thiourea derivative and copper(II) acetylacetonate.

The compositions according to the invention can moreover advantageously contain one or more organic or preferably inorganic fillers. Fibrous and in particular particulate fillers are preferred. Filler-containing compositions are particularly suitable as dental fixing cements or filling composites.

Glass fibres, carbon fibres, ceramic and aramid fibres as well as nanofibres or whiskers are preferred as fibrous fillers. Fibrous fillers are particularly suitable for the preparation of composite materials. By nanofibres is meant fibres with a length of less than 100 nm and by whiskers is meant needle-shaped single crystals, preferably made of aluminium oxide or silicon carbide. Whiskers typically have a diameter of a few μm and a length of up to 1 mm.

Preferred particulate fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as pyrogenic silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide.

Preferably, the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, glass powders with a particle size of from 0.2 to 1.5 μm, in particular radiopaque glass powders of e.g. barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

Unless otherwise indicated, all particle sizes are weight-average particle sizes (D50 values), wherein the particle size determination in the range of from 0.1 μm to 1000 μm is preferably effected by means of static light scattering, for example using an LA-960 Static Laser Scattering Particle Size Analyzer (Horiba, Japan). Here, a laser diode with a wavelength of 655 nm and an LED with a wavelength of 405 nm are used as light sources. The use of two light sources with different wavelengths makes it possible to measure the entire particle size distribution of a specimen in only one measurement pass, wherein the measurement is carried out as a wet measurement. For this purpose, a 0.1 to 0.5% aqueous dispersion of the filler is prepared and the scattered light thereof is measured in a flow cell. The scattered light analysis for calculating particle size and particle size distribution is effected in accordance with the Mie theory according to DIN/ISO 13320. The measurement of the particle size in the range of from 5 nm to 0.1 μm is preferably effected by dynamic light scattering (DLS) of aqueous particle dispersions, preferably using an He—Ne laser with a wavelength of 633 nm, at a scattering angle of 90° and at 25° C., e.g. using a Malvern Zetasizer Nano ZS (Malvern Instruments, Malvern UK).

Particle sizes smaller than 0.1 μm can also be determined by means of SEM or TEM micrographs. Transmission electron microscopy (TEM) is preferably carried out using a Philips CM30 TEM at an accelerating voltage of 300 kV. For the preparation of the specimens, drops of the particle dispersion are applied to a 50 Å thick copper grid (mesh size 300 mesh), which is coated with carbon, and then the solvent is evaporated. The particles are counted and the arithmetic mean is calculated.

The fillers are divided according to their particle size into macrofillers and microfillers, wherein fillers with an average particle size of from 0.2 to 15 μm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splinter-shaped particles. Microfillers such as mixed oxides can be prepared e.g. by hydrolytic co-condensation of metal alkoxides.

To improve the bond between the filler particles and the crosslinked polymerization matrix, the fillers are preferably surface-modified. $SiO_2$-based fillers are preferably surface-modified with methacrylate-functionalized silanes, particularly preferably with 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxydecyl dihydrogen phosphate, can also be used.

Moreover, the dental materials according to the invention can contain one or more further additives, above all stabilizers, colorants, microbiocidal active ingredients, fluoride-ion-releasing additives, propellants, optical brighteners, plasticizers and/or UV absorbers.

The materials according to the invention preferably contain:
a) 0.5 to 70 wt.-%, preferably 1 to 60 wt.-% and particularly preferably 3 to 50 wt.-% of at least one compound of formula I,
b) 0.01 to 5 wt.-%, preferably 0.1 to 3.0 wt.-% and particularly preferably 0.1 to 1.0 wt.-% of at least one initiator for the radical polymerization, preferably a photoinitiator,
c) 1 to 70 wt.-%, preferably 1.5 to 60 wt-% and particularly preferably 2 to 50 wt.-% of at least one radically polymerizable comonomer,
d) 0 to 85 wt.-% of at least one filler.

All quantities specified herein are relative to the total mass of the composition, unless otherwise indicated.

The filling level depends on to the desired application of the material. Filling composites preferably have a filler content of from 50 to 85 wt.-%, particularly preferably 70 to 80 wt.-%, and dental cements have a filler content of from 10 to 70 wt.-%, particularly preferably 60 to 70 wt.-%.

Those dental materials which consist of the named components are particularly preferred, wherein the individual components are preferably selected in each case from the above-named preferred and particularly preferred substances.

The compositions according to the invention are particularly suitable as dental materials, in particular as dental cements, filling composites and veneering materials and also as materials for producing prostheses, artificial teeth, inlays, onlays, crowns and bridges. The compositions are suitable primarily for intraoral application by the dentist for the restoration of damaged teeth, i.e. for therapeutic application, e.g. as dental cements, filling composites and veneering materials. However, they can also be used non-therapeutically (extraorally), for example in the production or repair of dental restorations, such as prostheses, artificial teeth, inlays, onlays, crowns and bridges.

The compositions according to the invention are moreover suitable for the production of shaped bodies for dental, but also for non-dental purposes, which can be produced e.g. by means of casting, compression moulding and in particular by additive processes such as 3D printing.

Another subject-matter of the invention is the use of a compound according to formula I for the preparation of a radically polymerizable material, preferably a medical and in particular a dental material.

The invention is explained in more detail in the following with reference to embodiment examples.

EMBODIMENT EXAMPLES

Example 1

Synthesis of 2,2',4,4',6,6'-hexaethyl-O'4,O4-(hexane-1,6-diyl)bis(hepta-1,6-diene-2,4,4,6-tetracarboxylate) (1)

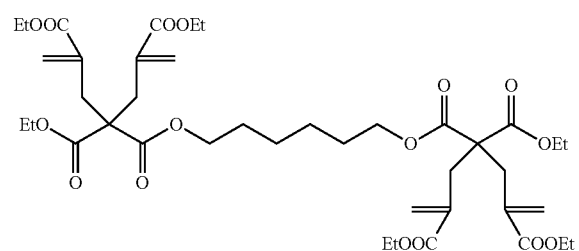

1st stage: Synthesis of diethyl-O,O'-(hexane-1,6-diyl) dimalonate (ZP-1)

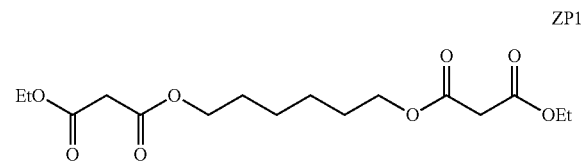 [SMILES: CCOC(=O)CC(=O)OCCCCCCOC(=O)CC(=O)OCC]

1,6-Hexanediol (42.3 mmol, 5.00 g) was dissolved in dry dichloromethane (DCM, 150 ml) and the apparatus was flushed with argon. The solution was cooled in ice water, after which first pyridine (105.8 mmol, 8.37 g) and then ethyl malonyl chloride (105.8 mmol, 15.93 g) were added. The solution was stirred at room temperature for 4 h and subsequently quenched with 1N HCl (150 ml). The aqueous phase was extracted 3 times with DCM (150 ml), the combined organic phases were washed with saturated NaHCO$_3$ solution (150 ml) and dried over anhydrous Na$_2$SO$_4$. The solvent was distilled off, the coloured crude product was filtered over silica gel (eluent PE:EA 4:1) and thus the pure product ZP1 was obtained as a colourless oil in a yield of 12.35 g (84% theoretical).

$^1$H-NMR: (400 MHz, CDCl$_3$) δ (ppm): 4.10 (8H, m, O—CH$_2$—), 3.29 (4H, s, C—CH$_2$—C), 1.59 (4H, m, CH$_2$), 1.32 (4H, m, CH$_2$), 1.28 (6H, m, —CH$_3$).

2nd stage: Synthesis of 2,2'4,4'6,6'-hexaethyl-O'4, O4-(hexane-1,6-diyl) bis (hepta-1,6-diene-2,4,4,6-tetracarboxylate) (1)

Sodium hydride (60 wt.-%, suspension in mineral oil, 178.3 mmol, 4.28 g) was placed in a three-necked flask and the apparatus was flushed with argon. Dry tetrahydrofuran (THF) (100 ml) was added and the reaction solution was cooled in an ice bath. ZP1 from stage 1 (35.7 mmol, 12.35 g) was slowly added dropwise and the reaction solution was stirred for 2 h at room temperature. After addition of ethyl chloromethylacrylate (146.2 mmol, 21.72 g) it was stirred overnight and then quenched with saturated NH$_4$Cl solution (100 ml). The aqueous phase was extracted 3 times with diethyl ether (100 ml) and the combined organic phases were dried over anhydrous sodium sulfate. After evaporation of the solvent, the crude product was purified by means of column chromatography (PE:EA 4:1) and the pure product was obtained as a viscous liquid in a yield of 21.95 g (77% theoretical).

$^1$H-NMR: (400 MHz, CDCl$_3$) δ (ppm): 6.25 (4H, s, C=CH$_2$), 5.68 (4H, s, C=CH$_2$), 4.22-3.96 (16H, m, O—CH$_2$—), 2.95 (8H, s, C—CH$_2$—C), 1.57 (4H, m), 1.26 (22H, m).

$^{13}$C-NMR: (100 MHz, CDCl$_3$) δ (ppm): 170.5 (C=O), 170.4 (C=O), 167.1 (C=O), 136.3 (C4), 128.7 (C2), 65.4 (C2), 61.5 (C2), 61.0 (C2), 57.6 (C4), 34.9 (C2), 28.4 (C2), 25.6 (C2), 14.3 (C1), 14.0 (C1).

Example 2 (Comparison Example)

Synthesis of diethyl-2,2'-(oxybis(methylene)) diacylate (2)

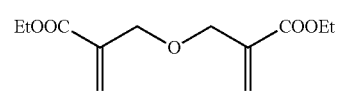

2

The synthesis of compound 2 was carried out based on Tsuda et al., Polymer, 35 (1994), 3317-3328:

Ethyl acrylate (149.8 mmol, 15.0 g), paraformaldehyde (149.8 mmol, 4.5 g) and 1,4-diazabicyclo(2.2.2)octane (1 g) were placed in a three-necked flask and this solution was stirred for 3 days at 95° C. After the solution had been cooled, 200 ml petroleum ether was added and the solution was washed 3 times with 100 ml 3% HCl and once with 100 ml water. The organic phase was dried over anhydrous sodium sulfate and the solvent was removed. The crude product was purified by means of column chromatography and obtained as a colourless oil in a yield of 11.7 g (65% theoretical).

$^1$H-NMR: (400 MHz, CDCl$_3$) δ (ppm): 6.30 (2H, s, C=CH$_2$), 5.88 (2H, s, C=CH$_2$), 4.31-4.13 (8H, m, O—CH$_2$—), 1.29 (6H, t).

$^{13}$C-NMR: (100 MHz, CDCl$_3$) δ (ppm): 165.9 (C=O), 137.4 (C4), 125.7 (C2), 69.0 (C2), 60.9 (C2), 14.3 (C1).

Example 3

2,2' 4,4' 6,6'-Hexaethyl-O'$^4$,O$^4$-{[(propane-2,2-diyl-bis(4,1-phenylene))bisoxy]bis-(propane-1,2-diyl)}-bis(hepta-1,6-diene-2,4,4,6-tetracarboxylate), Isomer Mixture (3)

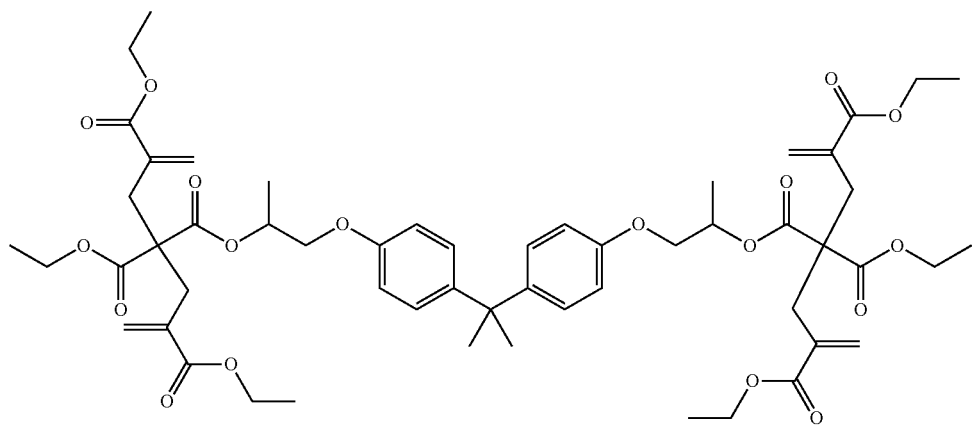

3

1st Stage: O,O'-{[(Propane-2,2-diylbis-4,1-phenylene)-bisoxy]bis(propane-1,2-diyl)}-dimalonic Acid Diethyl Ester, Isomer Mixture (ZP-2)

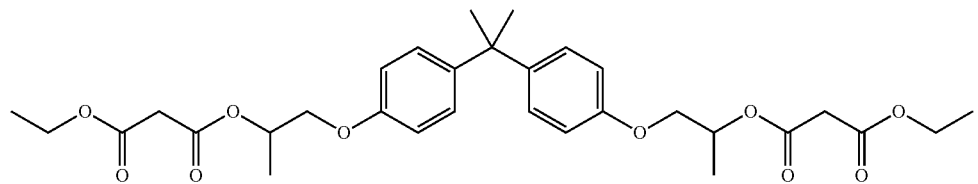

ZP-2

Pyridine (9.89 g; 0.125 mol) and subsequently, accompanied by ice cooling, ethyl malonyl chloride (18.82 g; 0.125 mol) were added dropwise to a solution of 1,1'-{[propane-2,2-diylbis(4,1-phenylene)]bis(oxy)}bis(propane-2-ol) (isomer mixture, 17.22 g, 50.0 mmol) in DCM (100 ml) and the reaction mixture was stirred at ambient temperature. After 4 h, hydrochloric acid (1N; 100 ml) was added and the phases were separated. The aqueous phase was extracted with DCM (3×50 ml). The combined organic phases were washed with saturated aqueous sodium hydrogen carbonate solution (100 ml) and saturated aqueous sodium chloride solution (100 ml), dried over anhydrous sodium sulfate, filtered and concentrated on a rotary evaporator. After purification of the crude product by means of column chromatography (SiO$_2$, n-heptane/ethyl acetate 3:1), 21.30 g (37.2 mmol; 74% theoretical) of a yellowish oil was obtained.

$^1$H-NMR (CDCl$_3$, 400 MHz): δ (main isomer)=7.12 (4H, m; Ar—H), 6.79 (4H, m; Ar—H), 5.29 (2H, m; O—CH), 4.18 (4H, m; O—CH$_2$), 3.98 (4H, m; O—CH$_2$), 3.36 (4H, s; CH$_2$), 1.62 (6H, s; CH$_3$), 1.37 (6H, d; CH—CH$_3$; J=6.5 Hz), 1.25 (6H, t; CH$_3$; J=7.1 Hz).

$^{13}$C-NMR (CDCl$_3$, 100.6 MHz): δ (main isomer)=166.3 (C=O), 166.0 (C=O), 156.2 (Ar—C), 143.4 (Ar—C), 127.6 (Ar—CH), 113.8 (Ar—CH), 70.0 (O—CH$_2$), 69.6 (O—CH$_2$), 61.4 (O—CH), 41.6 (CH$_2$), 41.5 (C), 30.9 (CH$_3$), 16.4 (CH$_3$), 13.9 (CH$_3$).

2nd stage: 2,2',4,4',6,6'-Hexaethyl O'$^4$,O$^4$-{[(propane-2,2-diylbis(4,1-phenylene))bisoxy]bis-(propane-1,2-diyl)}-bis(hepta-1,6-diene-2,4,4,6-tetracarboxylate), isomer mixture (3)

A solution of ZP-2 (21.05 g, 36.8 mmol) in THF (50 ml) was added dropwise at 0° C. to a suspension of sodium hydride (4.42 g, 0.184 mol) in THF (100 ml) and the reaction mixture was stirred at ambient temperature. After 3 h, a solution of 2-chloromethylacrylic acid ethyl ester (22.39 g, 0.151 mol) in THF (50 ml) was added dropwise, accompanied by ice cooling. The reaction mixture was stirred for 24 h at ambient temperature, then saturated aqueous ammonium chloride solution (100 ml) was added dropwise. Water (100 ml) and ethyl acetate (250 ml) were added and the phases were separated. The aqueous phase was extracted with ethyl acetate (2×80 ml). The combined organic phases were washed with saturated aqueous sodium chloride solution (2×80 ml), dried over anhydrous sodium sulfate and filtered. The filtrate was concentrated on a rotary evaporator. After purification of the crude product by means of column chromatography (SiO$_2$, n-heptane/ethyl acetate 3:1), 30.82 g (30.2 mmol; 82% theoretical) of a highly viscous colourless oil was obtained. $^1$H-NMR (CDCl$_3$, 400 MHz): δ (main isomer)=7.11 (4H, m; Ar—H), 6.77 (4H, m; Ar—H), 6.27 (4H, m; =CH), 5.74 (4H, m; =CH), 5.20 (2H, m; O—CH), 4.15 (8H, m; O—CH$_2$), 4.11-3.88 (8H, m; O—CH$_2$), 3.07-2.91 (8H, m; CH$_2$), 1.62 (6H, s; CH$_3$), 1.34 (6H, d; CH—CH$_3$; J=6.5 Hz), 1.28 (6H, t; CH$_3$; J=7.1 Hz), 1.18 (6H, t; CH$_3$; J=7.1 Hz).

$^{13}$C-NMR (CDCl$_3$, 100.6 MHz): δ (main isomer)=170.1 (C=O), 169.7 (C=O), 166.9 (C=O), 156.2 (Ar—C), 143.3 (Ar—C), 136.0 (=C), 135.8 (=C), 128.6 (=CH$_2$), 128.3 (=CH$_2$), 127.6 (Ar—CH), 113.7 (Ar—CH), 70.1 (O—CH), 69.3 (O—CH$_2$), 61.3 (O—CH$_2$), 60.8 (O—CH$_2$), 60.7 (O—CH$_2$), 57.4 (C), 41.5 (C), 34.3 (CH$_2$), 34.1 (CH$_2$), 30.9 (CH$_3$), 16.2 (CH$_3$), 14.0 (CH$_2$), 13.7 (CH$_3$).

Example 4

2,2',4,4'6,6'-Hexaethyl-O'$^4$,O$^4$-[(octahydro-1H-4,7-methanoindene-2,5-diyl)bis(methylene)-bis(hepta-1,6-diene-2,4,4,6-tetracarboxylate), Isomer Mixture (4)

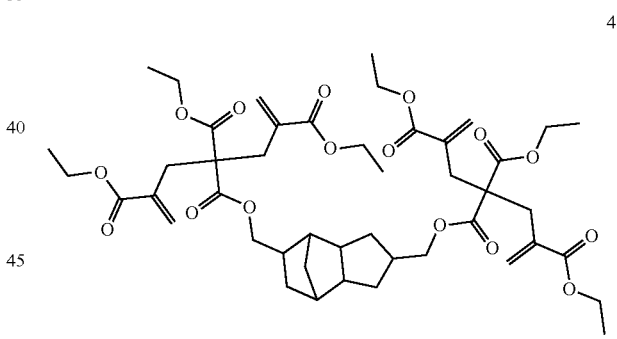

4

1st stage: O,O'-[(Octahydro-1H-4,7-methanoindene-2,5-diyl)bis(methylene)]-dimalonic Acid Diethyl Ester, Isomer Mixture (ZP-3)

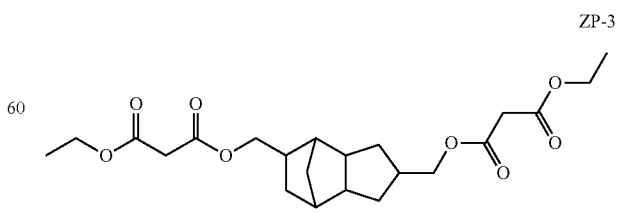

ZP-3

Pyridine (9.89 g; 0.125 mol) and subsequently, accompanied by ice cooling, ethyl malonyl chloride (18.82 g; 0.125 mol) were added dropwise to a solution of 4,8-bis(hydroxymethyl)tricyclo[5.2.1.0²,⁶]decane, isomer mixture (9.81 g, 50.0 mmol) in DCM (100 ml) and the reaction mixture was stirred at ambient temperature. After 4 h, hydrochloric acid (1N; 100 ml) was added and the phases were separated. The aqueous phase was extracted with dichloromethane (3×50 ml). The combined organic phases were washed with saturated aqueous sodium hydrogen carbonate solution (100 ml) and saturated aqueous sodium chloride solution (100 ml), dried over anhydrous sodium sulfate, filtered and concentrated on a rotary evaporator. After purification of the crude product by means of column chromatography ($SiO_2$, n-heptane/ethyl acetate 1:1), 20.75 g (48.9 mmol; 98% theoretical) of a yellowish oil was obtained.

$^1$H-NMR ($CDCl_3$, 400 MHz): δ=4.25-4.16 (4H, m; O—$CH_2$), 4.04-3.87 (4H, m; O—$CH_2$), 3.40-3.34 (4H, m; $CH_2$), 2.56-1.32 (14H, m), 1.29 (6H, t; $CH_3$; J=7.2 Hz).

$^{13}$C-NMR ($CDCl_3$, 100.6 MHz): δ=166.5 (C=O), 166.4 (C=O), 166.3 (C=O), 69.6 (O—$CH_2$), 69.0 (O—$CH_2$), 68.6 (O—$CH_2$), 68.6 (O—$CH_2$), 61.3 (O—$CH_2$), 49.1 (CH), 48.6 (CH), 45.3 (CH), 44.7 (CH), 44.6 (CH), 44.3 (CH), 43.5 (CH), 42.8 (CH), 42.5 (CH), 41.5 ($CH_2$), 41.3 (CH), 40.8 (CH), 40.5 (CH), 40.2 ($CH_2$), 40.0 (C), 39.2 ($CH_2$), 38.5 (CH), 37.9 (CH), 33.9 (CH), 33.8 (CH), 33.0 (CH), 32.3 ($CH_2$), 32.1 ($CH_2$), 30.5 ($CH_2$), 30.1 ($CH_2$), 27.9 ($CH_2$), 27.5 ($CH_2$), 25.0 ($CH_2$), 24.2 ($CH_2$), 13.9 ($CH_3$).

2nd stage: 2,2',4,4',6,6'-Hexaethyl-O'⁴,O⁴-[(octahydro-1H-4,7-methanoindene-2,5-diyl)bis(methylene)]-bis(hepta-1,6-diene-2,4,4,6-tetracarboxylate), isomer mixture (4)

A solution of ZP-3, isomer mixture (20.45 g, 48.2 mmol) in THF (50 ml) was added dropwise at 0° C. to a suspension of sodium hydride (5.78 g, 0.241 mol) in tetrahydrofuran (100 ml) and the reaction mixture was stirred at ambient temperature. After 3 h, a solution of 2-chloromethylacrylic acid ethyl ester (29.35 g, 0.198 mol) in THF (50 ml) was added dropwise, accompanied by ice cooling. The reaction mixture was stirred for 24 h at ambient temperature, then saturated aqueous ammonium chloride solution (100 ml) was added dropwise. Water (100 ml) and ethyl acetate (250 ml) were added and the phases were separated. The aqueous phase was extracted with ethyl acetate (2×80 ml). The combined organic phases were washed with saturated aqueous sodium chloride solution (2×80 ml), dried over anhydrous sodium sulfate and filtered. The filtrate was concentrated on a rotary evaporator. After purification of the crude product by means of column chromatography ($SiO_2$, n-heptane/ethyl acetate 3:1), 30.30 g (34.7 mmol; 72% theoretical) of a highly viscous yellowish oil was obtained.

$^1$H-NMR ($CDCl_3$, 400 MHz): δ=6.31-6.19 (4H, m; =CH), 5.74-5.61 (4H, m; =CH), 4.23-4.07 (12H, m; O—$CH_2$), 3.91-3.73 (4H, m; O—$CH_2$), 3.04-2.82 (8H, m; $CH_2$), 2.56-1.34 (14H, m), 1.33-1.21 (18H, m; $CH_3$).

$^{13}$C-NMR ($CDCl_3$, 100.6 MHz): δ=170.3 (C=O), 170.2 (C=O), 170.1 (C=O), 168.7 (C=O), 168.6 (C=O), 166.8 (C=O), 166.1 (C=O), 136.6 (=C), 136.0 (=C), 135.9 (=C), 128.4 (=$CH_2$), 127.5 (=$CH_2$), 69.1 (O—$CH_2$), 68.9 (O—$CH_2$), 68.6 (O—$CH_2$), 68.5 (O—$CH_2$), 61.3 (O—$CH_2$), 60.7 (O—$CH_2$), 57.3 (C), 50.8 (CH), 50.7 (CH), 48.8 (CH), 45.4 (CH), 44.7 (CH), 44.4 (CH), 43.5 (CH), 42.9 (CH), 42.8 (CH), 41.2 (CH), 40.9 (CH), 40.8 (CH), 40.2 ($CH_2$), 40.1 (CH), 39.2 ($CH_2$), 38.3 (CH), 38.0 (CH), 34.7 ($CH_2$), 34.6 ($CH_2$), 33.8 (CH), 33.6 (CH), 32.9 (CH), 32.4 ($CH_2$), 31.3 ($CH_2$), 30.5 ($CH_2$), 27.9 ($CH_2$), 27.4 ($CH_2$), 24.3 ($CH_2$), 14.0 ($CH_3$), 13.9 ($CH_3$), 13.8 ($CH_3$).

Example 5

Photopolymerization and Determination of the Volume Contraction

The volume contraction during the polymerization (polymerization shrinkage) $\Delta V_P$ of the monomer 1 according to the invention from Example 1 (Example 5, B1) was measured by means of density measurement before and after the polymerization and compared with the commercially available reference monomer 1,10-decanediol dimethacrylate ($D_3MA$, CAS: 6701-13-9) (Example 5: comparison example V1). $D_3MA$ was used as reference because it likewise has an alkylene spacer between the polymerizable groups and has the same interatomic distance as 1. In addition the already known (cf.: U.S. Pat. No. 5,145,374) cyclopolymerizable monomer 2 from Example 2 was used as reference monomer (Example 5: comparison example V2). The density of the monomers was determined by means of a 1-ml pycnometer, while the density of the cured polymers was determined by means of Archimedes' principle. 1 mol % BMDG (bis(4-methoxybenzoyl)-diethylgermanium) as photoinitiator was added to the monomers, which were poured into a silicone mould (15×10×4 mm) and cured using a light furnace (Lumamat 100 model, Ivoclar AG, 400-500 nm, 20 mW cm$^{-2}$) in each case for 10 min per side.

TABLE 1

Polymerization shrinkage $\Delta V_P$ of the monomer 1 according to the invention as well as of the comparison compounds D3MAa and monomer 2

| Example | Monomer | $\rho_{monomer}$ [g/mL] | $\rho_{polymer}$ [g/mL] | $\Delta V_P$ [vol.-%] |
|---|---|---|---|---|
| V1 | $D_3MA$ | 0.962 | 1.091 | 12.8 |
| V2 | 2 | 1.055 | 1.220 | 12.2 |
| B1 | 1 | 1.127 | 1.194 | 4.4 |

The results in Table 1 prove that the monomer 1 according to the invention surprisingly displays a much lower polymerization shrinkage than the analogous dimethacrylate monomer $D_3MA$ and the cyclopolymerizable monomer 2 known from the state of the art and thus represents a clear advantage for dimensionally accurate applications that are to keep their shape as much as possible.

Example 6

Reactivity Measurement by Means of RT-NIR Photorheometry

In order to investigate the photoreactivity and above all the polymerization-induced shrinkage force of the monomer 1 according to the invention, the prepared formulations B1, V1 and V2 from Example 5 were measured using an MCR302 WESP real-time near-infrared (RT-NIR) photorheometer from Anton Paar, which was coupled to a Bruker Vertex 80 IR spectrometer to monitor conversion. A PP-25 measuring system was used, and the measuring gap was set to 0.2 mm. Before and during curing (10 mW·cm$^{-2}$ on specimen surface; 400-500 nm; Omnicure 2000), the storage and loss moduli of the specimens were measured in oscillation mode (1% deflection, 1 Hz). At the same time, IR spectra of the specimen were recorded during the measurement at a frequency of ~4 Hz. The reaching of the gel point (intersection of storage and loss moduli) and the time taken to reach 95% of the final double-bond conversion ($t_{95\%}$) were used as a measure of the photoreactivity. In addition, the conversion at the gel point ($DBC_g$), the total conversion (DBC) and the photopolymerization-induced shrinkage stress (Fs) were determined. The results obtained are summarized in Table 2.

TABLE 2

Results of the reactivity measurements with monomer 1 and the reference monomers 2 and $D_3MA$

| Example | Monomer | Gel point [s] | $DBC_g$ [%] | DBC [%] | $t_{95\%}$ [s] | Fs [N] |
|---|---|---|---|---|---|---|
| V1 | $D_3MA$ | 6.2 | 12 | 83 | 71 | −36 |
| V2 | 2 | 14.8 | 23 | 77 | 87 | −35 |
| B1 | 1 | 4.1 | 13 | 77 | 116 | −21 |

If the gel point of the monomers is considered, it can be seen that the monomer 1 reaches it, at 4.1 s, much faster than the reference compounds $D_3MA$ and monomer 2. This demonstrates a high reactivity of monomer 1. The conversion at the gel point, by contrast, is similarly low in the case of $D_3MA$ and monomer 1 at 12-13%. The cyclopolymerizable reference monomer 2 displays a much higher conversion at the gel point (23%), which can be explained by the partial cyclopolymerization and thus lack of crosslinking. The final conversion varies around ~80% both in the case of monomer 1 and the comparison compounds 2 and $D_3MA$, wherein $D_3MA$ reaches a slightly higher DBC. This is to be attributed to a higher flexibility of the long alkylene chain, whereas monomer 1 and to some extend also reference compound 2 form rigid ring structures during the polymerization and are thus clearly at an advantage in particular at the start of the polymerization. In the case of the monomer 1 according to the invention the shrinkage force occurring during the polymerization is over a third lower, at −21 N, than in the case of the reference substance $D_3MA$ at −36 N. This shows the clear advantage of monomer 1 compared with the conventional dimethacrylate. The results surprisingly show that the likewise cyclopolymerizable comparison monomer 2 also has a very high shrinkage force, which makes it clear that the compound 1 according to the invention has substantial advantages compared with the known comparison compound.

Example 7

Copolymerization of Monomer 1 with Dimethacryalte Comonomers

In order to demonstrate the ability of the monomer 1 according to the invention to copolymerize, in each case one component of a base resin formulation (equimolar mixture of the commercially available dimethacrylates urethane dimethacrylate (UDMA, isomer mixture; CAS: 72869-86-4) and 1,10-decanediol dimethacrylate ($D_3MA$)) was replaced by an equimolar quantity of the monomer 1 or of the reference monomer 2 and the reactivity and occurring shrinkage force were investigated by means of RT-NIR photorheometry. In each case 1 mol % BMDG (bis(4-methoxybenzoyl)-diethylgermanium) was added to the mixtures as photoinitiator and the RT-NIR photorheometry measurements were carried out analogously to Example 6.

TABLE 3

Results of the reactivity measurements of the copolymers

| Example | Monomer mixture | Gel point [s] | $DBC_g$ [%] | DBC [%] | $t_{95\%}$ [S] | $F_S$ [N] |
|---|---|---|---|---|---|---|
| V3 | $D_3MA$-UDMA | 1.5 | 16 | 78 | 79 | −32 |
| V4 | $D_3MA$-2 | 9.3 | 12 | 84 | 94 | −42 |
| V5 | UDMA-2 | 2.4 | 16 | 79 | 88 | −33 |
| B2 | $D_3MA$-1 | 3.2 | 10 | 83 | 112 | −29 |
| B3 | UDMA-1 | 3.0 | 18 | 75 | 82 | −23 |

The results in Table 3 prove the good copolymerization of monomer 1 both with the low-viscosity $D_3MA$ and with the viscous UDMA. Although the copolymerization with $D_3MA$ leads to a gel point that is 1.7 s later, it is much faster than the copolymerization of reference monomer 2 with $D_3MA$ (9.3 s). The gelling of the copolymerizations with UDMA is within the same range in the case of the monomers 1 and 2, wherein monomer 2 gels 0.6 s faster. Both the final conversion (~80%) and $t_{95\%}$ (~90 s) lie in the same range in the case of all 5 formulations. If the occurring shrinkage force is considered, the great advantage of monomer 1 is seen again. Whereas the reference mixture V3 has a shrinkage force of −32 N, the substitution of $D_3MA$ with monomer 1 leads to a shrinkage force of only −23 N. If, by contrast, the reference monomer 2 is used, there is no reduction in the shrinkage force in the case of copolymerization with UDMA and an increase in the shrinkage force to −42 N is even observed in the case of the copolymerization with $D_3MA$. It could thus be demonstrated that the copolymerization of monomer 1 with dimethacrylates barely involves a reduction in the reactivity, but displays the advantage of a significant shrinkage force reduction. Although reference monomer 2, as a cyclopolymerizable monomer, likewise displayed a high reactivity with dimethacrylates, it effects about an increase in the occurring shrinkage force and is thus clearly at a disadvantage compared with monomer 1.

The invention claimed is:
1. A dental Dental-material, which comprises at least one compound of formula I,

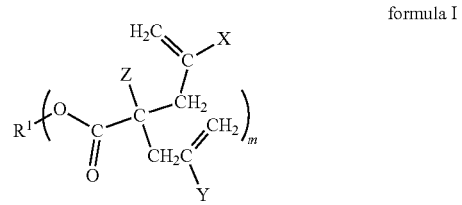

formula I in which
R¹ is an m-valent, linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein the aliphatic hydrocarbon radicals can be interrupted by one or more urethane groups, ester groups, oxygen atoms and/or sulfur atoms,
X,Y,Z independently of each other in each case are —COOR², —CON(R³R⁴), an aromatic $C_6$-$C_{10}$ hydrocarbon radical or —CN, wherein
R²,R³,R⁴ in each case independently of each other is hydrogen, a linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein aliphatic hydrocarbon radicals can be interrupted by one or more oxygen atoms, and m is 2 or 3.

2. The dental material according to claim 1, wherein the variables have the following meanings:
$R^1$ a linear, branched or cyclic aliphatic $C_1$-$C_{20}$ hydrocarbon radical, which can be interrupted by one or more urethane groups, ester groups and/or oxygen atoms,
X,Y,Z independently of each other in each case —$COOR^2$, an aromatic $C_6$-$C_{10}$ hydrocarbon radical or —CN,
$R^2$ a linear, branched or cyclic aliphatic $C_1$-$C_{10}$ hydrocarbon radical, which can be interrupted by one or more oxygen atoms, and
m 2 or 3.

3. The dental material according to claim 1, wherein the variables have the following meanings:
$R^1$ a linear, branched or cyclic aliphatic $C_1$-$C_{20}$ hydrocarbon radical, which can be interrupted by 1 to 3 urethane groups, ester groups and/or oxygen atoms,
X,Y,Z independently of each other in each case —$COOR^2$, an aromatic $C_6$-$C_{10}$ hydrocarbon radical or —CN,
$R^2$ a linear, branched or cyclic aliphatic $C_1$-$C_{10}$ hydrocarbon radical, which can be interrupted by 1 to 3 oxygen atoms, and
m 2 or 3.

4. The dental material according to claim 1, wherein the variables have the following meanings:
$R^1$ a linear, branched or cyclic, aliphatic $C_1$-$C_{12}$ hydrocarbon radical which can be interrupted by 1 to 3 oxygen atoms or is not interrupted,
X,Y,Z independently of each other in each case —$COOR^2$ or phenyl,
$R^2$ a linear or branched $C_1$-$C_4$ hydrocarbon radical, and
m 2 or 3.

5. The dental material according to claim 1, wherein the variables have the following meanings:
$R^1$ a saturated, branched or linear $C_2$ to $C_8$ hydrocarbon radical, which can be interrupted by 1 to 3 oxygen atoms or is not interrupted,
X,Y,Z —$COOR^2$,
$R^2$ ethyl, and
m 2.

6. The dental material according to one of claim 1, which additionally comprises at least one further polymerizable monomer.

7. The dental material according to claim 6, wherein the at least one further polymerizable monomer is a radically polymerizable mono- or multifunctional (meth)acrylate.

8. The dental material according to claim 7, which comprises one or more multifunctional monomers as further polymerizable monomer, selected from bisphenol A dimethacrylate, 2,2-bis[4-(2-hydroxy-3-methacryloyloxypropyl)phenyl]propane (bis-GMA), ethoxylated or propoxylated bisphenol A dimethacrylate, 2,2-bis[4-(2-methacryloyloxypropoxy)phenyl]propane, 1,6-bis-[2-methacryloyloxyethoxycarbonylamino]-2,2,4-trimethylhexane (UDMA), di-, tri- or tetraethylene glycol dimethacrylate, trimethylolpropane trimethacrylate, pentaerythritol tetramethacrylate, glycerol di- or glycerol trimethacrylate, 1,4-butanediol dimethacrylate, 1,10-decanediol dimethacrylate ($D_3MA$), 1,12-dodecanediol dimethacrylate, bis(methacryloyloxymethyl)tricyclo-[5.2.1.0$^{2,6}$]decane (DCP) or a mixture thereof.

9. The dental material according to one of claim 7, which comprises one or more monofunctional monomers as further polymerizable monomer, selected from benzyl methacrylate, tetrahydrofurfuryl methacrylate, isobornyl methacrylate, p-cumyl-phenoxyethylene glycol methacrylate (CMP-1E), 2-(2-biphenyloxy)-ethyl methacrylate or a mixture thereof.

10. The dental material according to one of claim 6, which comprises 0.5 to 70 wt.-% of at least one compound of formula I, and/or in total a maximum of 70 wt.-% multifunctional comonomers, and/or in total a maximum of 10 wt.-% monofunctional comonomers, in each case relative to the total mass of the material.

11. The dental material according to claim 6, which comprises 3 to 50 wt.-% of at least one compound of formula I, and/or 2 to 50 wt.-% multifunctional methacrylates, and/or in total a maximum of 5 wt.-% monofunctional methacrylates, in each case relative to the total mass of the material.

12. The dental material according to claim 6, which comprises one or more multifunctional acrylates as further polymerizable monomer, selected from ethylene glycol diacrylate, hexanediol diacrylate, tripropylene glycol diacrylate, ethoxylated bisphenol A diacrylate, polyethylene glycol 200 diacrylate, trimethylolpropane triacrylate, pentaerythritol tetraacrylate or a mixture thereof.

13. The dental material according to one of claim 1, which additionally comprises at least one initiator for the radical polymerization by UV light, by visible light, a thermal initiator and/or a redox initiator.

14. The dental material according to one of claim 1, which additionally comprises at least one inorganic filler.

15. The dental material according to one of claim 1, which comprises a) 0.5 to 70 wt.-% of at least one compound of formula I, b) 0.01 to 5 wt.-% of at least one initiator comprising a photoinitiator, c) 1 to 70 wt.-% of at least one radically polymerizable comonomer, d) 0 to 85 wt.-% of at least one filler, in each case relative to the total mass of the material.

16. The dental material according to claim 1, which comprises a) 3 to 50 wt.-% of at least one compound of formula I, b) 0.1 to 1.0 wt.-% of at least one initiator comprising a photoinitiator, c) 2 to 50 wt.-% of at least one radically polymerizable comonomer, d) 0 to 85 wt.-% of at least one filler, in each case relative to the total mass of the material.

17. The dental material according to claim 15, which comprises 50 to 85 wt.-% filler.

18. The dental material according to claim 16, which comprises 60 to 70 wt.-% filler.

19. The dental material according to claim 1 for therapeutic use as dental cement, filling composite, coating or veneering material.

20. A medical material, which comprises at least one compound of formula I,

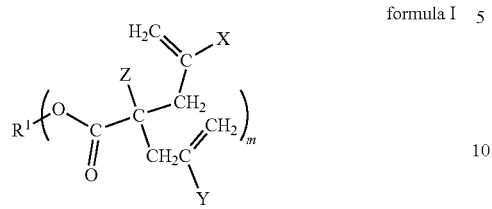

formula I in which

R¹ is an m-valent, linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein the aliphatic hydrocarbon radicals can be interrupted by one or more urethane groups, ester groups, oxygen atoms and/or sulfur atoms, X,Y,Z independently of each other in each case are —COOR², —CON(R³R⁴), an aromatic $C_6$-$C_{10}$ hydrocarbon radical or —CN, wherein R²,R³,R⁴ in each case independently of each other is hydrogen, a linear, branched or cyclic aliphatic $C_1$-$C_{30}$ hydrocarbon radical or an aromatic $C_6$-$C_{30}$ hydrocarbon radical, wherein the aliphatic or aromatic hydrocarbon radical can be substituted or unsubstituted and wherein aliphatic hydrocarbon radicals can be interrupted by one or more oxygen atoms, and m is 2 or 3.

* * * * *